(12) United States Patent
Nakaie

(10) Patent No.: US 10,141,517 B2
(45) Date of Patent: Nov. 27, 2018

(54) CHARGE-TRANSPORTING MATERIAL

(71) Applicant: NISSAN CHEMICAL INDUSTRIES, LTD., Tokyo (JP)

(72) Inventor: Naoki Nakaie, Funabashi (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 0 days.

(21) Appl. No.: 15/328,366

(22) PCT Filed: Jul. 22, 2015

(86) PCT No.: PCT/JP2015/070758
§ 371 (c)(1),
(2) Date: Jan. 23, 2017

(87) PCT Pub. No.: WO2016/013556
PCT Pub. Date: Jan. 28, 2016

(65) Prior Publication Data
US 2017/0213981 A1 Jul. 27, 2017

(30) Foreign Application Priority Data
Jul. 24, 2014 (JP) ................................. 2014-150768

(51) Int. Cl.
| | | |
|---|---|---|
| *H01L 51/50* | (2006.01) | |
| *H01L 51/56* | (2006.01) | |
| *C09K 11/06* | (2006.01) | |
| *C09D 5/24* | (2006.01) | |
| *C07C 255/35* | (2006.01) | |
| *H01L 51/00* | (2006.01) | |
| *C07D 403/14* | (2006.01) | |

(52) U.S. Cl.
CPC ........ *H01L 51/0061* (2013.01); *C07C 255/35* (2013.01); *C07D 403/14* (2013.01); *C09D 5/24* (2013.01); *C09K 11/06* (2013.01); *H01L 51/50* (2013.01); *H01L 51/0003* (2013.01); *H01L 51/0067* (2013.01); *H01L 51/0072* (2013.01); *H01L 51/5088* (2013.01); *H01L 51/56* (2013.01)

(58) Field of Classification Search
None
See application file for complete search history.

(56) References Cited

U.S. PATENT DOCUMENTS

| | | |
|---|---|---|
| 2008/0029742 A1 | 2/2008 | Yoshimoto et al. |
| 2010/0159279 A1 | 6/2010 | Kato et al. |
| 2010/0230639 A1 | 9/2010 | Yamada et al. |
| 2017/0005272 A1 | 1/2017 | Nakaie et al. |

FOREIGN PATENT DOCUMENTS

| | | |
|---|---|---|
| EP | 2 339 659 A1 | 6/2011 |
| JP | 2015-92560 A | 5/2015 |
| WO | WO 2006/025342 A1 | 3/2006 |
| WO | WO 2008/032616 A1 | 3/2008 |
| WO | WO 2008/129947 A1 | 10/2008 |
| WO | WO 2010/058777 A1 | 5/2010 |
| WO | WO 2012/140905 A1 | 10/2012 |
| WO | WO 2013-163710 A | 8/2013 |
| WO | WO 2015/137395 A1 | 9/2015 |

OTHER PUBLICATIONS

Extended European Search Report dated Dec. 20, 2017, in European Patent Application No. 15825334.4.

*Primary Examiner* — Samantha L Shterengarts
(74) *Attorney, Agent, or Firm* — Birch, Stewart, Kolasch & Birch, LLP

(57) ABSTRACT

This charge-transporting material, which includes a charge-transporting substance, halo-tetracyanoquinodimethane, and a complexing agent comprising an amide compound such as 1,3-dimethyl-2-imidazolidinone, for example, and capable of forming a complex with halo-tetracyanoquinodimethane, and in which the halo-tetracyanoquinodimethane and complexing agent form a complex, makes it possible to provide a thin film having excellent charge-transporting properties and to realize an organic EL element having low drive voltage when said thin film is applied to a hole injection layer.

12 Claims, 3 Drawing Sheets

CHARGE-TRANSPORTING MATERIAL

TECHNICAL FIELD

Figure 1:
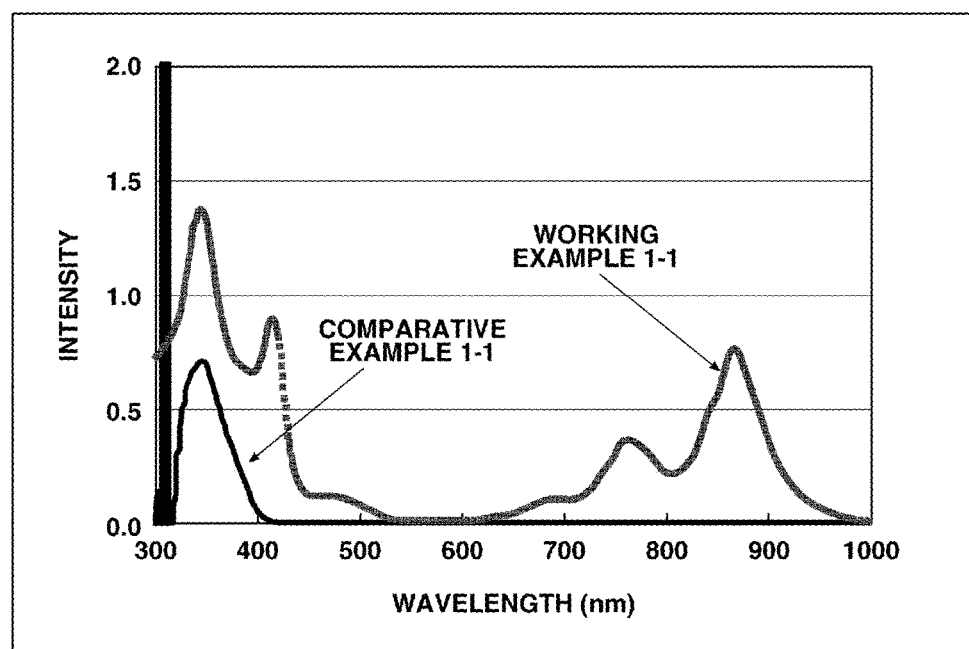

This invention relates to a charge-transporting material.

BACKGROUND ART

Charge-transporting thin films made of organic compounds are used as light-emitting layers and charge-injecting layers in organic electroluminescent (EL) devices. In particular, a hole-injecting layer is responsible for transferring charge between an anode and a hole-transporting layer or a light-emitting layer, and thus serves an important function in achieving low-voltage driving and high brightness in organic EL devices.

Processes for forming the hole-injecting layer are broadly divided into dry processes such as vapor deposition and wet processes such as spin coating. Comparing these different processes, wet processes are better able to efficiently produce thin films having a high flatness over a large area. Hence, with the advances being made today toward larger-area organic EL displays, there exists a desire for hole-injecting layers that can be formed by wet processes.

In view of these circumstances, the inventor and others have developed charge-transporting materials which can be used in various wet processes and which, when used to form a hole-injecting layer in an organic EL device, are capable of achieving excellent EL device characteristics. They have also developed, for use in such charge-transporting materials, compounds having a good solubility in organic solvents (see, for example, Patent Documents 1 to 4).

However, improvements in wet process materials for hole-injection layers are constantly being demanded. In particular, there is a desire for wet process materials which give thin films having an excellent charge transportability.

PRIOR ART DOCUMENTS

Patent Documents

Patent Document 1: WO 2008/032616
Patent Document 2: WO 2008/129947
Patent Document 3: WO 2006/025342
Patent Document 4: WO 2010/058777

SUMMARY OF THE INVENTION

Problems to be Solved by the Invention

It is therefore an object of this invention to provide a charge-transporting material which gives a thin film of excellent charge transportability and which also, when this thin film is used as a hole-injecting layer, enables an organic EL device having a low driving voltage to be achieved.

Means for Solving the Problems

The inventor has conducted extensive investigations in order to achieve this object, as a result of which he has discovered that a thin film obtained from a charge-transporting material prepared by adding a halotetracyanoquinodimethane-complexing agent to a composition which contains a charge-transporting substance and, as a dopant substance for the same, at least a halotetracyanoquinodimethane, has an excellent charge transportability. The inventor has also found that by using such a thin film as a hole-injecting layer in an organic EL device, a device having a low driving voltage can be obtained.

Accordingly, the invention provides:
1. A charge-transporting material comprising a charge-transporting substance, a halotetracyanoquinodimethane, and a complexing agent having the ability to form a complex with the halotetracyanoquinodimethane, wherein the halotetracyanoquinodimethane and the complexing agent form a complex;
2. The charge-transporting material of 1 above, wherein the complexing agent is an amide compound;
3. The charge-transporting material of 2 above, wherein the amide compound is 1,3-dimethyl-2-imidazolidinone;
4. The charge-transporting material of any of 1 to 3 above, wherein the halotetracyanoquinodimethane is 2,3,5,6-tetrafluoro-7,7,8,8-tetracyanoquinodimethane;
5. The charge-transporting material of any of 1 to 4 above which further comprises a heteropolyacid;
6. The charge-transporting material of any of 1 to 5 above, wherein the charge-transporting substance is a charge-transporting oligomer;
7. A charge-transporting thin film produced using the charge-transporting material of any of 1 to 6 above;
8. An organic electroluminescent device comprising the charge-transporting thin film of 7 above;
9. A method for producing a charge-transporting thin film, which method comprises the steps of applying the charge-transporting material of any of 1 to 6 above onto a substrate, and drying the applied material;
10. A method for enhancing the charge transportability of a charge-transporting thin film formed from a composition containing a charge-transporting substance and a halotetracyanoquinodimethane, the method being characterized by adding to the composition a complexing agent having the ability to form a complex with the halotetracyanoquinodimethane;
11. A method for enhancing the charge transportability of a charge-transporting thin film formed from a composition containing a charge-transporting substance, a halotetracyanoquinodimethane and an organic solvent, the method being characterized by using, as at least some portion of the organic solvent, a complexing agent having the ability to form a complex with the halotetracyanoquinodimethane;
12. The charge transportability-enhancing method of 10 or 11 above, wherein the complexing agent is an amide compound;
13. A halotetracyanoquinodimethane complexing agent consisting of an amide compound; and
14. An agent for enhancing the charge transportability of a charge-transporting thin-film containing a charge-transporting substance and a halotetracyanoquinodimethane, which agent consists of an amide compound.

Advantageous Effects of the Invention

The charge-transporting material of the invention includes a charge-transporting substance and, as a dopant substance, a halotetracyanoquinodimethane, and also includes a complexing agent having the ability to form a complex with the halotetracyanoquinodimethane. Because the halotetracyanoquinodimethane and the complexing agent together form a complex, this material provides thin films of excellent charge transportability. Although the reason for the improvement in charge transportability is not clear, it is presumed that the electrical characteristics improve as a result of interactions of some kind between complexing agent that remains within the thin film and the halotetracyanoquinodimethane.

Also, given that, in the charge-transporting material, the halotetracyanoquinodimethane forms a complex with the complexing agent, an additional advantage is an improvement in the storage stability of the charge-transporting material.

Thin films produced from the charge-transporting material of the invention can be suitably used as thin films for electronic devices such as organic EL devices. In particular, by employing such a thin film as the hole-injecting layer in an organic EL device, it is possible to obtain organic EL devices having a low driving voltage.

Moreover, the charge-transporting material of the invention can reproducibly form thin films of excellent charge transportability even when various wet processes capable of film formation over a large area, such as spin coating or slit coating, are used, and therefore is capable of fully accommodating recent advances in the field of organic EL devices.

BRIEF DESCRIPTION OF THE DIAGRAMS

Figure 2:
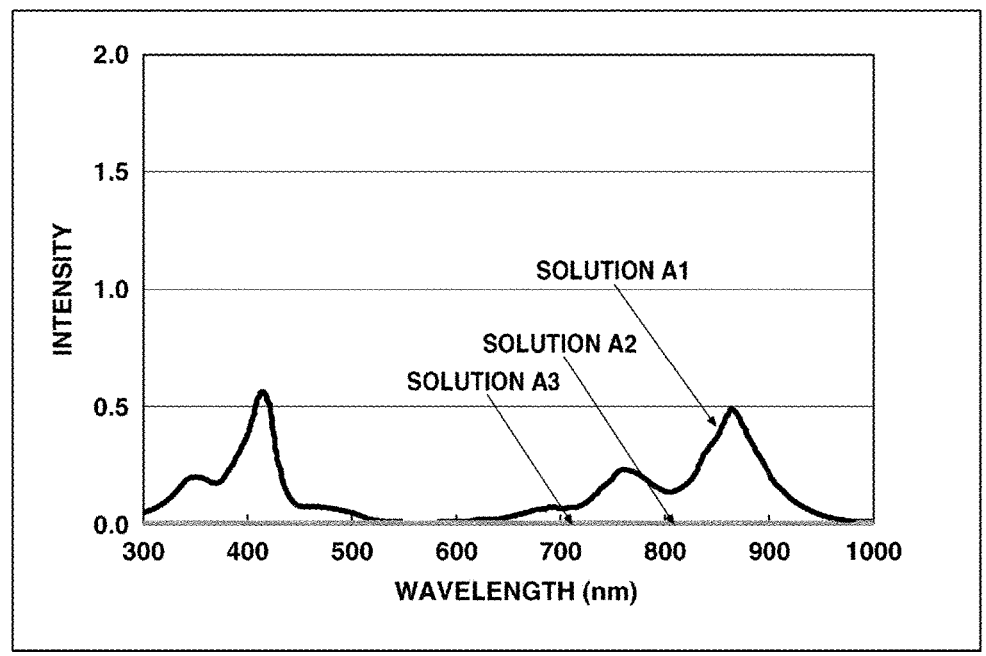
Figure 3:
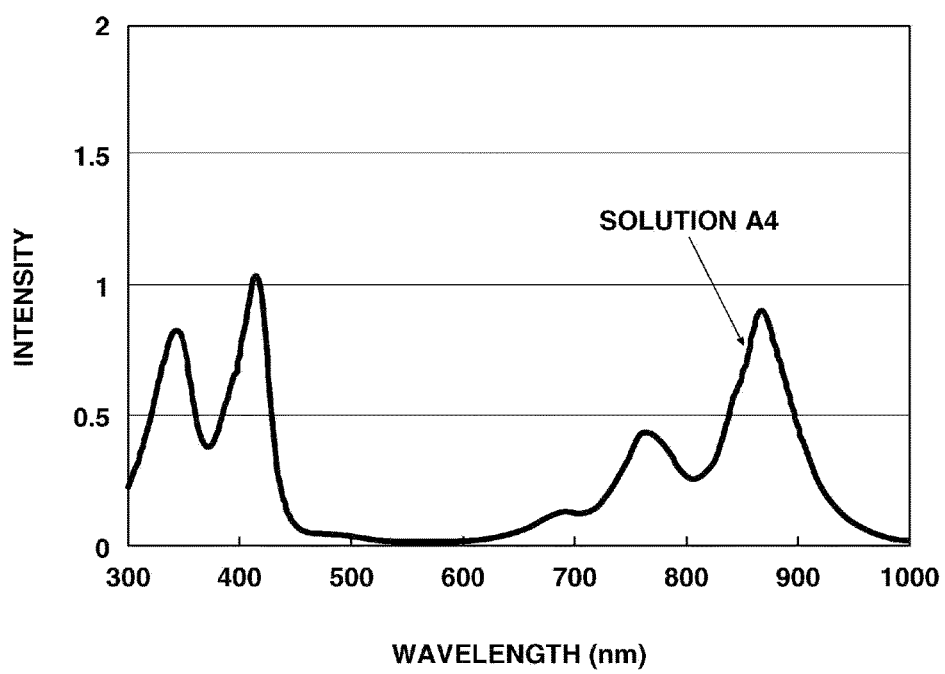
Figure 4:
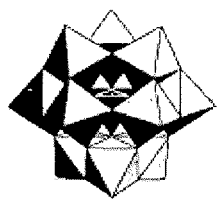
Figure 4:
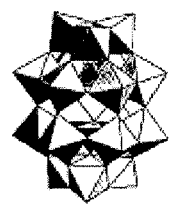

FIG. 1 shows a confocal laser microscopic image of the thin film produced in Working Example 2-1.
FIG. 2 shows a confocal laser microscopic image of the thin film produced in Working Example 2-2.
FIG. 3 shows a confocal laser microscopic image of the thin film produced in Comparative Example 2-1.
FIG. 4(A) refers to the Keggin-type chemical structure (D1).
FIG. 4(B) refers to the Dawson-type chemical structure (D2).

EMBODIMENT FOR CARRYING OUT THE INVENTION

The invention is described more fully below.

The charge-transporting material according to this invention includes a charge-transporting substance, a halotetracyanoquinodimethane, and a complexing agent having the ability to form a complex with the halotetracyanoquinodimethane. In the charge-transporting material, the halotetracyanoquinodimethane and the complexing agent form a complex.

The charge-transporting substance is not particularly limited, provided it is a substance that has charge transportability. Use can be made of charge-transporting compounds that have hitherto been used in, for example, the field of organic EL devices. Of these, charge-transporting compounds having a molecular weight of 200 to 9,000 are preferred.

The charge-transporting compound is exemplified by various hole-transporting substances, including arylamine derivatives such as oligoaniline derivatives, N,N'-diarylbenzidine derivatives and N,N,N',N'-tetraarylbenzidine derivatives; thiophene derivatives such as oligothiophene derivatives, thienothiophene derivatives and thienobenzothiophene derivatives; and pyrrole derivatives such as oligopyrrole derivatives. Of these, arylamine derivatives and thiophene derivatives are preferred, and arylamine derivatives are more preferred.

The charge-transporting substance may be one that has charge transportability itself, or one that exhibits charge transportability when used together with a dopant substance.

In the invention, the charge-transporting compound has a molecular weight which, as mentioned above, is preferably from 200 to 9,000. From the standpoint of obtaining a charge-transporting thin film having a high solvent resistance, the molecular weight is more preferably at least 300, and even more preferably at least 400. From the standpoint of preparing a uniform varnish that reproducibly gives thin films having a high flatness, the molecular weight is preferably not more than 8,000, more preferably not more than 7,000, even more preferably not more than 6,000, and still more preferably not more than 5,000.

To prevent separation of the charge-transporting substance when forming a thin film, it is preferable for the charge-transporting compound to have no molecular weight distribution (a polydispersity of 1); that is, it is preferable for the charge-transporting compound to have a single molecular weight.

The halotetracyanoquinodimethane compound is exemplified by compounds of formula (1).

[Chemical Formula 1]

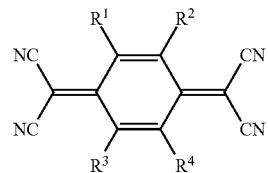

(1)

In the formula, $R^1$ to $R^4$ are each independently a hydrogen atom or a halogen atom, with at least one being a halogen atom, preferably at least two being halogen atoms, more preferably at least three being halogen atoms, and most preferably all being halogen atoms.

The halogen atom is exemplified by fluorine, chlorine, bromine and iodine atoms, with a fluorine atom or chlorine atom being preferred, and a fluorine atom being more preferred.

Illustrative examples of halotetracyanoquinodimethane compounds include
2,3,5,6-tetrafluoro-7,7,8,8-tetracyanoquinodimethane (F4TCNQ),
2,3,5,6-tetrachloro-7,7,8,8-tetracyanoquinodimethane,
2-fluoro-7,7,8,8-tetracyanoquinodimethane,
2-chloro-7,7,8,8-tetracyanoquinodimethane,
2,5-difluoro-7,7,8,8-tetracyanoquinodimethane and
2,5-dichloro-7,7,8,8-tetracyanoquinodimethane.
In this invention, F4TCNQ is most preferred.

The halotetracyanoquinodimethane compound content in the charge-transporting material of the invention, based on the charge-transporting substance, is preferably from 0.0001 to 1 equivalent, more preferably from 0.001 to 0.5 equivalent, and even more preferably from 0.01 to 0.2 equivalent.

In addition to the above halotetracyanoquinodimethane, other dopant substances may be used as the dopant substance in the charge-transporting material of the invention.

Use can be made of both inorganic dopant substances and organic dopant substances as such other dopant substances.

When the resulting thin film is used as a hole-injecting layer in an organic EL device, in order to reproducibly obtain devices having a long life, heteropolyacids are preferred as inorganic dopant substances. "Heteropolyacid" refers to a polyacid having a structure in which a heteroatom is positioned at the center of the molecule—typically the Keggin-type chemical structure shown in formula (D1) or the Dawson-type chemical structure shown in formula (D2), and which is obtained by the condensation of an isopolyacid that is an oxoacid of vanadium (V), molybdenum (Mo), tungsten (W) or the like with an oxoacid of a different element. Examples of such oxoacids of a different element include primarily oxoacids of silicon (Si), phosphorus (P) and arsenic (As).

[Chemical Formula 2]

Chemical Formula 2 is shown in FIG. 4(A) and FIG. 4(B) of the drawings.

Examples of heteropolyacids include phosphomolybdic acid, silicomolybdic acid, phosphotungstic acid, silicotungstic acid and phosphotungstomolybdic acid. These may be used singly, or two or more may be used in combination. The heteropolyacid used in this invention may be acquired as a commercial product or may be synthesized by a known method.

In particular, when one heteropolyacid is used, this one heteropolyacid is preferably phosphotungstic acid or phosphomolybdic acid, and most preferably phosphotungstic acid. When two or more heteropolyacids are used, one of the two or more heteropolyacids is preferably phosphotungstic acid or phosphomolybdic acid, and more preferably phosphotungstic acid.

Even a heteropolyacid having, in quantitative analysis such as elemental analysis, numbers for the elements which are higher or lower than in the structure indicated by the general formula may be used in this invention, provided it was acquired as a commercial product or was suitably synthesized according to a known method of synthesis.

For example, phosphotungstic acid is generally represented by the chemical formula $H_3(PW_{12}O_{40}) \cdot nH_2O$ and phosphomolybdic acid is generally represented by the chemical formula $H_3(PMo_{12}O_{40}) \cdot nH_2O$. In quantitative analysis, regardless of whether the numbers for the elements P (phosphorus), O (oxygen) and W (tungsten) or Mo (molybdenum) within these formulas are high or low, so long as the heteropolyacid was acquired as a commercial product or suitably synthesized by a known method of synthesis, it may be used in this invention. In such cases, the mass of the heteropolyacid specified in this invention refers not to the mass of pure phosphotungstic acid within the product of synthesis or the commercial product (phosphotungstic acid content), but rather, in the form that is available as a commercial product or the form that can be isolated by a known method of synthesis, to the total mass in a state that includes water of hydration and other impurities.

The heteropolyacid included in the charge-transporting material of the invention may be set to a mass ratio, relative to unity (1) for the charge-transporting substance, of about 1.0 to about 70.0, preferably about 2.0 to about 60.0, and more preferably about 2.5 to about 55.0.

Benzoquinone derivatives are preferred as organic dopant substances.

Specific examples of benzoquinone derivatives include tetrachloro-1,4-benzoquinone (chloranil) and 2,3-dichloro-5,6-dicyano-1,4-benzoquinone (DDQ).

These inorganic and organic dopant substances may be used singly, or two or more may be used in combination.

No limitation is imposed on complexing agents having the ability to form a complex with the halotetracyanoquinodimethane, provided they are substances having the ability to form a complex, although amide compounds are especially preferred.

Specific examples of amide compounds include amide compounds of 3 to 5 carbon atoms that are liquid at normal temperature, such as 1,3-dimethyl-2-imidazolidinone, N,N-dimethylformamide, N,N-diethylformamide, N,N-dimethylacetamide and N-methylpyrrolidone.

Of these, 1,3-dimethyl-2-imidazolidinone is preferred.

Because such amide compounds of 3 to 5 carbon atoms readily dissolve charge-transporting substances (especially charge-transporting compounds having a molecular weight of 200 to 9,000) and halotetracyanoquinodimethane compounds, they can function as complexing agents and as solvents for charge-transporting materials of the invention that are in the form of a solution (varnish). Therefore, by using such an amide compound, the charge-transporting material of the invention can be obtained as a varnish that gives thin films of excellent flatness.

It is possible to check for the presence or absence of complex formation by measuring the UV-Vis spectrum of the charge-transporting material. Specifically, when complex formation occurs, absorption at wavelengths of 600 to 1,000 nm and the existence of two conspicuous peaks within this range can be confirmed.

In this invention, although the amount of complexing agent used is not particularly limited, the mass ratio expressed as "halotetracyanoquinodimethane:complexing agent" may be set to from about 1:1 to about 1:100, preferably from about 1:5 to about 1:100, and more preferably from about 1:30 to about 1:100.

In cases where the complexing agent functions as a solvent, the charge-transporting material of the invention may be composed of a charge-transporting substance, a halotetracyanoquinodimethane, a complexing agent, and other dopant substances that may be optionally used. However, to maintain the solubility of the charge-transporting substance, etc. and for such reasons as to adjust the viscosity of the charge-transporting material, another organic solvent may also be included.

For example, other organic solvents that may be used are high-solvency solvents which can readily dissolve the charge-transporting substance and the dopant substance.

Examples of such high-solvency solvents include organic solvents such as cyclohexanone and diethylene glycol monomethyl ether. These solvents may be used singly or two or more may be used in admixture. The amount of use may be suitably set within a range of 1 to 90 wt % of the overall solvent while taking into consideration such factors as the degree to which complex formation is inhibited and the degree of solubility of the charge-transporting substance, etc.

Here, the term 'solvent' in "overall solvent" refers to, in cases where the complexing agent functions as a solvent, the sum of all of the complexing agent and all other solvents. In cases where the complexing agent does not function as a solvent, this refers to the sum of all other solvents. The same applies below.

A high-viscosity organic solvent having a viscosity at 25° C. of from 10 to 200 mPa·s, especially 35 to 150 mPa·s, and a boiling point at normal pressure (atmospheric pressure) of from 50 to 300° C., especially 150 to 250° C., may be used. The viscosity of the charge-transporting material is easily adjusted thereby, as a result of which it is possible to prepare a material which is suitable for the coating method and reproducibly gives thin films having a high flatness.

Illustrative examples of high-viscosity organic solvents include cyclohexanol, ethylene glycol, ethylene glycol diglycidyl ether, 1,3-octylene glycol, diethylene glycol, dipropylene glycol, triethylene glycol, tripropylene glycol, 1,3-butanediol, 2,3-butanediol, 1,4-butanediol, propylene glycol and hexylene glycol. These solvents may be used singly, or two or more may be mixed and used together.

The addition ratio of high-viscosity organic solvent is suitably set within a range of 1 to 90 wt % based on the overall solvent, while taking into account such factors as the degree to which complex formation is inhibited and the degree of solubility of the charge-transporting substance, etc.

Also, in order to enhance the substrate wettability, adjust the surface tension of the solvent, adjust the polarity and adjust the boiling point, propylene glycol monomethyl ether, ethylene glycol monobutyl ether, diethylene glycol diethyl ether, diethylene glycol dimethyl ether, diethylene glycol monoethyl ether acetate, diethylene glycol monobutyl ether acetate, dipropylene glycol monomethyl ether, propylene glycol monomethyl ether acetate, diethylene glycol monoethyl ether, diacetone alcohol, γ-butyrolactone, ethyl lactate and n-hexyl acetate or the like may be mixed together in a ratio of 1 to 90 wt % with respect to the overall solvent while taking into account such factors as the degree to which complex formation is inhibited and the degree of solubility of the charge-transporting substance, etc.

These solvents may be used singly, or two or more be made used in admixture.

The charge-transporting material of the invention has a viscosity which is suitably set in accordance with the thickness and other properties of the thin film to be produced and the solids concentration, but is generally from 1 to 50 mPa·s at 25° C.

The solids concentration of the charge-transporting material in this invention is suitably set while taking into account properties such as the viscosity and surface tension of the charge-transporting material, and the thickness of the thin film to be produced, but is generally from about 0.1 to about 10.0 wt %. To increase the ease of applying the charge-transporting material, the solids concentration is preferably from about 0.5 to about 5.0 wt %, and more preferably from about 1.0 to about 3.0 wt %.

A charge-transporting thin-film can be formed on a substrate by applying the above-described charge-transporting material onto a substrate and baking the applied material.

Methods of application include, but are not particularly limited to, dipping, spin coating, slit coating, transfer printing, roll coating, brush coating, ink-jet printing and spraying. It is preferable to adjust the viscosity and surface tension of the charge-transporting material according to the method of application.

When using the charge-transporting material of the invention, the baking atmosphere is not particularly limited. Thin films having a uniform film surface and a high charge transportability can be obtained not only in an open-air atmosphere, but even in an inert gas such as nitrogen or in a vacuum.

The baking temperature is suitably set in the range of about 100 to 260° C. while taking into account such factors as the intended use of the resulting thin film, the degree of charge transportability to be imparted to the thin film, and the type and boiling point of the solvent. When the thin film thus obtained is to be used as a hole-injecting layer in an organic EL device, the baking temperature is preferably from about 140 to about 250° C., and more preferably from about 145 to about 240° C.

During baking, a temperature change in two or more steps may be applied for such purposes as to achieve more uniform film formability or to induce the reaction to proceed on the substrate. Heating may be carried out using a suitable apparatus such as a hot plate or an oven.

The thickness of the charge-transporting thin film is not particularly limited. However, when the thin film is to be used as a hole-injecting layer in an organic EL device, a film thickness of from 5 to 200 nm is preferred. Methods for changing the film thickness include, for example, changing the solids concentration in the charge-transporting material and changing the amount of solution on the substrate during application.

The materials and method employed to fabricate an OLED device using the charge-transporting material of the invention are exemplified by, but not limited to, those described below.

The electrode substrate to be used is preferably cleaned beforehand by liquid washing with, for example, a cleaning agent, alcohol or pure water. When the substrate is an anode substrate, it is preferably subjected to surface treatment such as UV/ozone treatment or oxygen-plasma treatment just prior to use. However, surface treatment need not be carried out if the anode material is composed primarily of organic substances.

An example of a method for fabricating an OLED device in which a thin-film obtained from the charge-transporting material of the invention serves as a hole-injecting layer is described below.

In this method, a hole-injecting layer is formed on an electrode by applying the charge-transporting material of the invention onto an anode substrate, and baking the applied material. The workpiece is then introduced into a vacuum deposition system, where a hole-transporting layer, a light-emitting layer, an electron-transporting layer, an electron-transporting layer/hole-blocking layer and a cathode metal are vapor-deposited in this order to give an OLED device. Where necessary, an electron-blocking layer may be provided between the light-emitting layer and the hole-transporting layer.

Illustrative examples of anode materials include transparent electrodes such as indium-tin oxide (ITO) and indium-zinc oxide (IZO), and metal anodes made of a metal such as aluminum or an alloy of such a metal. An anode material on which planarizing treatment has been carried out is preferred. Use can also be made of polythiophene derivatives and polyaniline derivatives having high charge transportability.

Examples of other metals making up the metal anode include, but are not limited to, scandium, titanium, vanadium, chromium, manganese, iron, cobalt, nickel, copper, zinc, gallium, yttrium, zirconium, niobium, molybdenum, ruthenium, rhodium, palladium, cadmium, indium, scandium, lanthanum, cerium, praseodymium, neodymium, promethium, samarium, europium, gadolinium, terbium, dysprosium, holmium, erbium, thulium, ytterbium, hafnium, thallium, tungsten, rhenium, osmium, iridium, platinum, gold, titanium, lead, bismuth, and alloys thereof.

Specific examples of hole-transporting layer-forming materials include triarylamines such as
(triphenylamine) dimer derivatives,
[(triphenylamine) dimer] spirodimer,
N,N'-bis(naphthalen-1-yl)-N,N'-bis(phenyl)benzidine (α-NPD),
N,N'-bis(naphthalen-2-yl)-N,N'-bis(phenyl)benzidine,
N,N'-bis(3-methylphenyl)-N,N'-bis(phenyl)benzidine,
N,N'-bis(3-methylphenyl)-N,N'-bis(phenyl)-9,9-spirobifluorene,
N,N'-bis(naphthalen-1-yl)-N,N'-bis(phenyl)-9,9-spirobifluorene,
N,N'-bis(3-methylphenyl)-N,N'-bis(phenyl)-9,9-dimethylfluorene,
N,N'-bis(naphthalen-1-yl)-N,N'-bis(phenyl)-9,9-dimethylfluorene,
N,N'-bis(3-methylphenyl)-N,N'-bis(phenyl)-9,9-diphenylfluorene, N,N'-bis(naphthalen-1-yl)-N,N'-bis(phenyl)-9,9-diphenyl-fluorene,
N,N'-bis(naphthalen-1-yl)-N,N'-bis(phenyl)-2,2'-dimethylbenzidine,
2,2',7,7'-tetrakis(N,N-diphenylamino)-9,9-spirobifluorene,
9,9-bis[4-(N,N-bis-biphenyl-4-yl-amino)phenyl]-9H-fluorene,
9,9-bis[4-(N,N-bis-naphthalen-2-yl-amino)phenyl]-9H-fluorene,
9,9-bis[4-(N-naphthalen-1-yl-N-phenylamino)phenyl]-9H-fluorene,
2,2',7,7'-tetrakis[N-naphthalenyl(phenyl)amino]-9,9-spirobifluorene,
N,N'-bis(phenanthren-9-yl)-N,N'-bis(phenyl)benzidine,
2,2'-bis[N,N-bis(biphenyl-4-yl)amino]-9,9-spirobifluorene,
2,2'-bis(N,N-diphenylamino)-9,9-spirobifluorene,
di[4-(N,N-di(p-tolyl)amino)phenyl]cyclohexane,
2,2',7,7'-tetra(N,N-di(p-tolyl))amino-9,9-spirobifluorene,
N,N,N',N'-tetra-naphthalen-2-yl-benzidine,
N,N,N',N'-tetra(3-methylphenyl)-3,3'-dimethylbenzidine,
N,N'-di(naphthalenyl)-N,N'-di(naphthalen-2-yl)benzidine,
N,N,N',N'-tetra(naphthalenyl)-benzidine,
N,N'-di(naphthalen-2-yl)-N,N'-diphenylbenzidine-1-4-diamine,
$N^1,N^4$-diphenyl-$N^1,N^4$-di(m-tolyl)benzene-1,4-diamine,
$N^2,N^2,N^6,N^6$-tetraphenylnaphthalene-2,6-diamine,
tris(4-(quinolin-8-yl)phenyl)amine,
2,2'-bis(3-(N,N-di(p-tolyl)amino)phenyl)biphenyl,
4,4',4"-tris[3-methylphenyl(phenyl)amino]triphenylamine (m-MTDATA) and
4,4',4"-tris[1-naphthyl(phenyl)amino]triphenylamine (1-TNATA); and oligothiophenes such as
5,5"-bis-{4-[bis(4-methylphenyl)amino]phenyl}-2,2':5',2"-terthiophene (BMA-3T).

Specific examples of light-emitting layer-forming materials include tris(8-quinolinolate) aluminum(III) ($Alq_3$),
bis(8-quinolinolate) zinc(II) ($Znq_2$),
bis(2-methyl-8-quinolinolate)(p-phenylphenolate) aluminum(III) (BAlq),
4,4'-bis(2,2-diphenylvinyl)biphenyl,
9,10-di(naphthalen-2-yl)anthracene,
2-t-butyl-9,10-di(naphthalen-2-yl)anthracene,
2,7-bis[9,9-di(4-methylphenyl)-fluoren-2-yl]-9,9-di(4-methylphenyl)fluorene,
2-methyl-9,10-bis(naphthalen-2-yl)anthracene,
2-(9,9-spirobifluoren-2-yl)-9,9-spirobifluorene,
2,7-bis(9,9-spirobifluoren-2-yl)-9,9-spirobifluorene,
2-[9,9-di(4-methylphenyl)-fluoren-2-yl]-9,9-di(4-methylphenyl)fluorene,
2,2'-dipyrenyl-9,9-spirobifluorene,
1,3,5-tris(pyren-1-yl)benzene,
9,9-bis[4-(pyrenyl)phenyl]-9H-fluorene,
2,2'-bi(9,10-diphenylanthracene),
2,7-dipyrenyl-9,9-spirobifluorene,
1,4-di(pyren-1-yl)benzene,
1,3-di(pyren-1-yl)benzene,
6,13-di(biphenyl-4-yl)pentacene,
3,9-di(naphthalen-2-yl)perylene,
3,10-di(naphthalen-2-yl)perylene,
tris[4-(pyrenyl)-phenyl]amine,
10,10'-di(biphenyl-4-yl)-9,9'-bianthracene,
N,N'-di(naphthalen-1-yl)-N,N'-diphenyl[1,1':4',1":4",1'''-quaterphenyl]-4,4'''-diamine,
4,4'-di[10-(naphthalen-1-yl)anthracen-9-yl]biphenyl,
dibenzo{[f,f']-4,4',7,7'-tetraphenyl}diindeno[1,2,3-cd:1',2',3'-lm]perylene,
1-(7-(9,9'-bianthracen-10-yl)-9,9-dimethyl-9H-fluoren-2-yl)pyrene,
1-(7-(9,9'-bianthracen-10-yl)-9,9-dihexyl-9H-fluoren-2-yl)pyrene,
1,3-bis(carbazol-9-yl)benzene,
1,3,5-tris(carbazol-9-yl)benzene,
4,4',4"-tris(carbazol-9-yl)triphenylamine,
4,4'-bis(carbazol-9-yl)biphenyl (CBP),
4,4'-bis(carbazol-9-yl)-2,2'-dimethylbiphenyl,
2,7-bis(carbazol-9-yl)-9,9-dimethylfluorene,
2,2',7,7'-tetrakis(carbazol-9-yl)-9,9-spirobifluorene,
2,7-bis(carbazol-9-yl)-9,9-di(p-tolyl)fluorene,
9,9-bis[4-(carbazol-9-yl)-phenyl]fluorene,
2,7-bis(carbazol-9-yl)-9,9-spirobifluorene,
1,4-bis(triphenylsilyl)benzene,
1,3-bis(triphenylsilyl)benzene,
bis(4-N,N-diethylamino-2-methylphenyl)-4-methylphenylmethane,
2,7-bis(carbazol-9-yl)-9,9-dioctylfluorene,
4,4"-di(triphenylsilyl)-p-terphenyl,
4,4'-di(triphenylsilyl)biphenyl,
9-(4-t-butylphenyl)-3,6-bis(triphenylsilyl)-9H-carbazole,
9-(4-t-butylphenyl)-3,6-ditrityl-9H-carbazole,
9-(4-t-butylphenyl)-3,6-bis(9-(4-methoxyphenyl)-9H-fluoren-9-yl)-9H-carbazole,
2,6-bis(3-(9H-carbazol-9-yl)phenyl)pyridine,
triphenyl(4-(9-phenyl-9H-fluoren-9-yl)phenyl)silane,
9,9-dimethyl-N,N-diphenyl-7-(4-(1-phenyl-1H-benzo[d]imidazol-2-yl)phenyl-9H-fluoren-2-amine,
3,5-bis(3-(9H-carbazol-9-yl)phenyl)pyridine,
9,9-spirobifluoren-2-yl-diphenyl-phosphine oxide,
9,9'-(5-triphenylsilyl)-1,3-phenylene)bis(9H-carbazole),
3-(2,7-bis(diphenylphosphoryl)-9-phenyl-9H-fluoren-9-yl)-9-phenyl-9H-carbazole,
4,4,8,8,12,12-hexa(p-tolyl)-4H-8H-12H-12C-azadibenzo[cd,mn]-pyrene,
4,7-di(9H-carbazol-9-yl)-1,10-phenanthroline,
2,2'-bis(4-(carbazol-9-yl)phenyl)biphenyl,
2,8-bis(diphenylphosphoryl)dibenzo[b,d]thiophene,
bis(2-methylphenyl)diphenylsilane,
bis[3,5-di(9H-carbazol-9-yl)phenyl]diphenylsilane,
3,6-bis(carbazol-9-yl)-9-(2-ethyl-hexyl)-9H-carbazole,
3-(diphenylphosphoryl)-9-(4-(diphenylphosphoryl)phenyl)-9H-carbazole and
3,6-bis[(3,5-diphenyl)phenyl]-9-phenylcarbazole.

A light-emitting layer may be formed by co-vapor deposition of any of these materials with a light-emitting dopant.

Specific examples of light-emitting dopants include
3-(2-benzothiazolyl)-7-(diethylamino)coumarin,
2,3,6,7-tetrahydro-1,1,7,7-tetramethyl-1H,5H,11H-10-(2-benzothiazolyl)quinolidino[9,9a, 1gh]coumarin,
quinacridone, N,N'-dimethyl-quinacridone,
tris(2-phenylpyridine) iridium(III) ($Ir(ppy)_3$),
bis(2-phenylpyridine)(acetylacetonate) iridium(III) ($Ir(ppy)_2(acac)$),
tris[2-(p-tolyl)pyridine) iridium(III) ($Ir(mppy)_3$),
9,10-bis[N,N-di(p-tolyl)amino]anthracene,
9,10-bis[phenyl(m-tolyl)amino]anthracene,
bis[2-(2-hydroxyphenyl)benzothiazolate] zinc(II),
$N^{10},N^{10},N^{10'},N^{10'}$-tetra(p-tolyl)-9,9'-bianthracene-10,10'-diamine,
$N^{10},N^{10},N^{10'},N^{10'}$-tetraphenyl-9,9'-bianthracene-10,10'-diamine,
$N^{10},N^{10'}$-diphenyl-$N^{10},N^{10'}$-dinaphthalenyl-9,9'-bianthracene-10,10'-diamine,
4,4'-bis(9-ethyl-3-carbazovinylene)-1,1'-biphenyl,
perylene, 2,5,8,11-tetra-t-butylperylene, 1,4-bis[2-(3-N-ethylcarbazolyl)vinyl]benzene,
4,4'-bis[4-(di-p-tolylamino)styryl]biphenyl,
4-(di-p-tolylamino)-4'-[(di-p-tolylamino)styryl]stilbene,
bis[3,5-difluoro-2-(2-pyridyl)phenyl-(2-carboxypyridyl)] iridium(III),
4,4'-bis[4-(diphenylamino)styryl]biphenyl,
bis(2,4-difluorophenylpyridinato)tetrakis(1-pyrazolyl)borate iridium(III),
N,N'-bis(naphthalen-2-yl)-N,N'-bis(phenyl)-tris(9,9-dimethylfluorenylene),
2,7-bis{2-[phenyl(m-tolyl)amino]-9,9-dimethylfluoren-7-yl}-9,9-dimethyl-fluorene,
N-(4-((E)-2-(6((E)-4-(diphenylamino)styryl)naphthalen-2-yl)vinyl)phenyl)-N-phenylbenzenamine,
fac-iridium(III) tris(1-phenyl-3-methylbenzimidazolin-2-ylidene-C,C$^{2'}$),
mer-iridium(III) tris(1-phenyl-3-methylbenzimidazolin-2-ylidene-C,C$^{2'}$),
2,7-bis[4-(diphenylamino)styryl]-9,9-spirobifluorene,
6-methyl-2-(4-(9-(4-(6-methylbenzo[d]thiazol-2-yl)phenyl)anthracen-10-yl)phenyl)benzo[d]thiazole,
1,4-di[4-(N,N-diphenyl)amino]styrylbenzene,
1,4-bis(4-(9H-carbazol-9-yl)styryl)benzene,
(E)-6-(4-(diphenylamino)styryl)-N,N-diphenylnaphthalen-2-amine,
bis(2,4-difluorophenylpyridinato)(5-(pyridin-2-yl)-1H-tetrazolate) iridium(III),
bis(3-trifluoromethyl-5-(2-pyridyl)pyrazole)((2,4-difluorobenzyl)diphenylphosphinate iridium(III),
bis(3-trifluoromethyl-5-(2-pyridyl)pyrazolate)(benzyl-diphenylphosphinate) iridium(III),
bis(1-(2,4-difluorobenzyl)-3-methylbenzimidazolium)(3-(trifluoromethyl)-5-(2-pyridyl)-1,2,4-triazolate) iridium (III),
bis(3-trifluoromethyl-5-(2-pyridyl)pyrazolate)(4',6'-difluorophenylpyridinate) iridium(III),
bis(4',6'-difluorophenylpyridinato)(3,5-bis(trifluoromethyl)-2-(2'-pyridyl)pyrrolate) iridium(III),
bis(4',6'-difluorophenylpyridinato)(3-(trifluoromethyl)-5-(2-pyridyl)-1,2,4-triazolate) iridium (III),
(Z)-6-mesityl-N-(6-mesitylquinolin-2(1H)-ylidene)quinoline-2-amine-BF$_2$,
(E)-2-(2-(4-(dimethylamino)styryl)-6-methyl-4H-pyran-4-ylidene)malononitrile,
4-(dicyanomethylene)-2-methyl-6-julolidyl-9-enyl-4-H-pyran,
4-(dicyanomethylene)-2-methyl-6-(1,1,7,7-tetramethyljulolidyl-9-enyl)-4H-pyran,
4-(dicyanomethylene)-2-t-butyl-6-(1,1,7,7-tetramethyljulolidin-4-ylvinyl)-4H-pyran,
tris(dibenzoylmethane)phenanthroline europium(III), 5,6,11,12-tetraphenylnaphthacene,
bis(2-benzo[b]thiophen-2-yl-pyridine)(acetylacetonate) iridium(III),
tris(1-phenylisoquinoline) iridium(III),
bis(1-phenylisoquinoline)(acetylacetonate) iridium(III),
bis[1-(9,9-dimethyl-9H-fluoren-2-yl)isoquinoline]-(acetylacetonate) iridium(III),
bis[2-(9,9-dimethyl-9H-fluoren-2-yl)quinoline]-(acetylacetonate) iridium(III),
tris[4,4'-di-t-butyl-(2,2')-bipyridine] ruthenium(III) bis(hexafluorophosphate),
tris(2-phenylquinoline) iridium(III),
bis(2-phenylquinoline)(acetylacetonate) iridium(III),
2,8-di-t-butyl-5,11-bis(4-t-butylphenyl)-6,12-diphenyltetracene,
bis(2-phenylbenzothiazolate)(acetylacetonate) iridium(III),
platinum 5,10,15,20-tetraphenyltetrabenzoporphyrin,
osmium(II) bis(3-trifluoromethyl-5-(2-pyridine)pyrazolate) dimethylphenylphosphine,
osmium(II) bis(3-trifluoromethyl)-5-(4-t-butylpyridyl)-1,2,4-triazolate)diphenylmethylphosphine,
osmium(II) bis(3-(trifluoromethyl)-5-(2-pyridyl)-1,2,4-triazole)dimethylphenylphosphine,
osmium(II) bis(3-(trifluoromethyl)-5-(4-t-butylpyridyl)-1,2,4-triazolate)dimethylphenylphosphine,
bis[2-(4-n-hexylphenyl)quinoline](acetylacetonate) iridium (III),
tris[2-(4-n-hexylphenyl)quinoline] iridium(III),
tris[2-phenyl-4-methylquinoline] iridium(III),
bis(2-phenylquinoline)(2-(3-methylphenyl)pyridinate) iridium(III),
bis(2-(9,9-diethyl-fluoren-2-yl)-1-phenyl-1H-benzo[d]-imidazolato)(acetylacetonate) iridium(III),
bis(2-phenylpyridine)(3-(pyridin-2-yl)-2H-chromen-9-onate) iridium(III),
bis(2-phenylquinoline)(2,2,6,6-tetramethylheptane-3,5-dionate) iridium(III),
bis(phenylisoquinoline)(2,2,6,6-tetramethylheptane-3,5-dionate) iridium(III),
iridium(III) bis(4-phenylthieno[3,2-c]pyridinato-N,C$^{2'}$)-acetylacetonate,
(E)-2-(2-t-butyl-6-(2-(2,6,6-trimethyl-2,4,5,6-tetrahydro-1H-pyrrolo[3,2,1-ij]quinolin-8-yl)vinyl)-4H-pyran-4-ylidene)-malononitrile,
bis(3-trifluoromethyl-5-(1-isoquinolyl)pyrazolate)(methyl-diphenylphosphine) ruthenium,
bis[(4-n-hexylphenyl)isoquinoline](acetylacetonate) iridium(III),
platinum(II) octaethylporphin,
bis(2-methyldibenzo[f,h]quinoxaline)(acetylacetonate) iridium(III) and
tris[(4-n-hexylphenyl)isoquinoline] iridium(III).

Specific examples of electron-transporting layer/hole-blocking layer-forming materials include
lithium 8-hydroxyquinolinate,
2,2',2"-(1,3,5-benzinetriyl)-triyl)-tris(1-phenyl-1-H-benzimidazole),
2-(4-biphenyl)-5-(4-t-butylphenyl)-1,3,4-oxadiazole,
2,9-dimethyl-4,7-diphenyl-1,10-phenanthroline,
4,7-diphenyl-1,10-phenanthroline,
bis(2-methyl-8-quinolinolate)-4-(phenylphenolato)aluminum,
1,3-bis[2-(2,2'-bipyridin-6-yl)-1,3,4-oxadiazo-5-yl]benzene,
6,6'-bis[5-(biphenyl-4-yl)-1,3,4-oxadiazo-2-yl]-2,2'-bipyridine,
3-(4-biphenyl)-4-phenyl-5-t-butylphenyl-1,2,4-triazole,
4-(naphthalen-1-yl)-3,5-diphenyl-4H-1,2,4-triazole,
2,9-bis(naphthalen-2-yl)-4,7-diphenyl-1,10-phenanthroline,
2,7-bis[2-(2,2'-bipyridin-6-yl)-1,3,4-oxadiazo-5-yl]-9,9-dimethylfluorene,
1,3-bis[2-(4-t-butylphenyl)-1,3,4-oxadiazo-5-yl]benzene,
tris(2,4,6-trimethyl-3-(pyridin-3-yl)phenyl)borane,
1-methyl-2-(4-(naphthalen-2-yl)phenyl)-1H-imidazo[4,5f][1,10]-phenanthroline,
2-(naphthalen-2-yl)-4,7-diphenyl-1,10-phenanthroline, phenyldipyrenylphosphine oxide,
3,3',5,5'-tetra[(m-pyridyl)-phen-3-yl]biphenyl,
1,3,5-tris[(3-pyridyl)-phen-3-yl]benzene,
4,4'-bis(4,6-diphenyl-1,3,5-triazin-2-yl)biphenyl,
1,3-bis[3,5-di(pyridin-3-yl)phenyl]benzene,
bis(10-hydroxybenzo[h]quinolinato)beryllium,
diphenylbis(4-(pyridin-3-yl)phenyl)silane and
3,5-di(pyren-1-yl)pyridine.

Specific examples of electron-injecting layer-forming materials include lithium oxide ($Li_2O$), magnesium oxide (MgO), alumina ($Al_2O_3$), lithium fluoride (LiF), sodium fluoride (NaF), magnesium fluoride ($MgF_2$), cesium fluoride (CsF), strontium fluoride ($SrF_2$), molybdenum trioxide ($MoO_3$), aluminum, Li(acac), lithium acetate and lithium benzoate.

Specific examples of cathode materials include aluminum, magnesium-silver alloys, aluminum-lithium alloys, lithium, sodium, potassium and cesium.

A specific example of an electron-blocking layer-forming material is tris(phenylpyrazole)iridium.

Methods for fabricating PLED devices using the charge-transporting material of the invention are exemplified by, but not particularly limited to, the following.

A PLED device having a charge-transporting thin film formed using the charge-transporting material of the invention can be produced by, in the fabrication of an OLED device as described above, successively forming a hole-transporting polymer layer and a light-emitting polymer layer instead of carrying out vacuum evaporation operations for a hole-transporting layer, a light-emitting layer, an electron-transporting layer and an electron-injecting layer.

Specifically, the charge-transporting material of the invention is applied onto an anode substrate, and a hole-injecting layer is formed by the above-described method. A hole-transporting polymer layer and a light-emitting polymer layer are then successively formed thereon, following which a cathode material is vapor-deposited on top, thereby giving an PLED device.

The cathode and anode materials used here may be similar to those used during the above-described fabrication of an OLED device, and similar cleaning treatment and surface treatment may be carried out.

The method of forming the hole-transporting polymer layer and the light-emitting polymer layer is exemplified by a film-forming method that entails adding a solvent to a hole-transporting polymer material or a light-emitting polymer material, or to the material obtained by adding a dopant substance to these, thereby dissolving or uniformly dispersing the material, and then applying the resulting solution or dispersion onto, respectively, the hole-injecting layer or the hole-transporting polymer layer and subsequently baking the applied layer.

Examples of hole-transporting polymer materials include
poly[(9,9-dihexylfluorenyl-2,7-diyl)-co-(N,N'-bis{p-butylphenyl}-1,4-diaminophenylene)],
poly[(9,9-dioctylfluorenyl-2,7-diyl)-co-(N,N'-bis{p-butylphenyl}-1,1'-biphenylene-4,4-diamine)],
poly[(9,9-bis{1'-penten-5'-yl}fluorenyl-2,7-diyl)-co-(N,N'-bis{p-butylphenyl}-1,4-diaminophenylene)],
poly[N,N'-bis(4-butylphenyl)-N,N'-bis(phenyl)-benzidine] end-capped with polysilsesquioxane and
poly[(9,9-dioctylfluorenyl-2,7-diyl)-co-(4,4'-(N-(p-butylphenyl))diphenylamine)].

Examples of light-emitting polymer materials include polyfluorene derivatives such as poly(9,9-dialkylfluorene) (PDAF), poly(phenylene vinylene) derivatives such as poly (2-methoxy-5-(2'-ethylhexoxy)-1,4-phenylene vinylene) (MEH-PPV), polythiophene derivatives such as poly(3-alkylthiophene) (PAT), and polyvinylcarbazole (PVCz).

Examples of the solvent include toluene, xylene and chloroform. Examples of the method of dissolution or uniform dispersion include stirring, stirring under applied heat, and ultrasonic dispersion.

Examples of the coating method include, but are not particularly limited to, inkjet printing, spraying, dipping, spin coating, transfer printing, roll coating and brush coating. Coating is preferably carried out in an inert gas atmosphere such as nitrogen or argon.

Examples of the baking method include methods that involve heating in an oven or on a hot plate, either within an inert gas atmosphere or in a vacuum.

EXAMPLES

Synthesis Examples, Working Examples and Comparative Examples are given below to more concretely illustrate the invention, although the invention is not limited by these Examples. The equipment used was as follows.
(1) $^1$H-NMR:
    JNM-ECP300 FT NMR System, from JEOL Ltd.
(2) Measurement of UV-Vis Spectra of Varnish:
    UV-3100 PC UV-visible spectrophotometer (Shimadzu Corporation)
(3) Substrate Cleaning:
    Substrate cleaning machine (reduced-pressure plasma system), from Choshu Industry Co., Ltd.
(4) Varnish Coating:
    MS-A100 Spin Coater, from Mikasa Co., Ltd.
(5) Film Thickness Measurement:
    Surfcorder ET-4000 microfigure measuring instrument, from Kosaka Laboratory, Ltd.
(6) EL Device Fabrication:
    C-E2L1G1-N Multifunction Vapor Deposition System, from Choshu Industry Co., Ltd.
(7) Measurement of EL Device Brightness:
    I-V-L Measurement System from Tech World, Inc.

[1] Compound Synthesis

[Synthesis Example 1] Synthesis of Arylamine Derivative 1 (AN1)

[Chemical Formula 3]

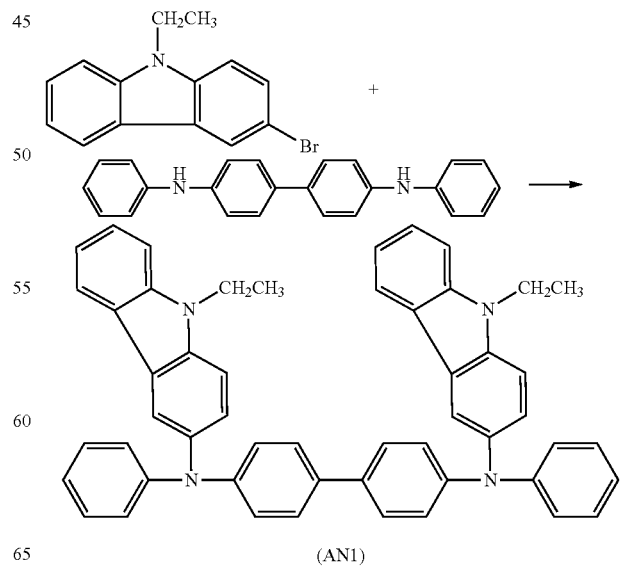

(AN1)

A reaction vessel was charged with 1.00 g of N,N'-diphenylbenzidine, 1.96 g of 3-bromo-9-ethylcarbazole, 34.7 mg of Pd(dba)$_2$ and 0.860 g of t-BuONa and then purged with nitrogen, after which 15 mL of toluene and 0.51 mL of a separately prepared toluene solution of P(t-Bu)$_3$ (concentration, 47.2 g/L) were added and the system was stirred for 6.5 hours at 50° C. to effect the reaction. After cooling to room temperature, toluene and a saturated saline solution were added and liquid-liquid extraction was carried out. The resulting organic phase was dried over Na$_2$SO$_4$, following which activated carbon was added and the system was stirred for 30 minutes at room temperature. The activated carbon was removed by filtration and then concentrated, and the resulting concentrate was added dropwise to a MeOH/AcOEt mixed solvent and the system was stirred under room temperature. The resulting slurry solution was filtered, after which it was dried and then again slurry-washed with a toluene-methanol mixed solvent. The powder obtained following filtration was dried, giving AN1 (amount, 1.87 g; yield, 87%). The $^1$H-NMR measurement results are shown below.

$^1$H-NMR (300 MHz, DMSO-d6) δ [ppm]:
8.10 (d, 3=7.8 Hz, 2H), 7.99 (d, 3=1.8 Hz, 2H), 7.59-7.66 (m, 4H), 7.42-7.51 (m, 6H), 7.23-7.29 (m, 7H), 6.94-7.18 (m, 11H).

[2] Preparation of Charge-Transporting Material

Working Example 1-1

A charge-transporting material (varnish) was prepared by dissolving 0.143 g of AN1, 0.416 g of phosphotungstic acid (PTA) and 0.273 g of F4TCNQ in 14.0 g of the complexing agent 1,3-dimethyl-2-imidazolidinone (DMI) under a nitrogen atmosphere, adding 4.0 g of 2,3-butanediol (2,3-BD) and 2.0 g of dipropylene glycol monomethyl ether (DPM) to the resulting solution, and stirring.

Comparative Example 1-1

A charge-transporting material (varnish) was prepared by dissolving 0.143 g of AN1, 0.416 g of PTA and 0.273 g of F4TCNQ in 20 g of cyclohexanone (CHN) under a nitrogen atmosphere, and stirring the resulting solution.

[3] Measurement of UV-Vis Spectrum of Varnish

The varnishes prepared in Working Example 1-1 and Comparative Example 1-1 were each diluted 1,000-fold on a weight basis. A mixed solvent (DMI: 2,3-BD DPM=70: 20:10) was used to dilute the Working Example 1-1 varnish, and cyclohexanone was used to dilute the Comparative Example 1-1 varnish. In addition, the UV-Vis spectra (wavelength, 300 to 1,000 nm; the same applies below) of the respective diluted varnishes were measured. The results are shown in FIG. 1.

The UV-Vis spectra of Solutions A1 to A4 prepared by the following methods were measured. The results are shown in FIG. 2 (Solution A1 to Solution A3) and FIG. 3 (Solution A4).

(1) Solution A1
Solution A1 was prepared by dissolving 0.068 g of F4TCNQ in 3.5 g of DMI under a nitrogen atmosphere, then adding 1.0 g of 2,3-BD and 0.5 g of DPM to the resulting solution and stirring.

(2) Solution A2
Solution A2 was prepared by dissolving 0.104 g of PTA in 3.5 g of DMI under a nitrogen atmosphere, then adding 1.0 g of 2,3-BD and 0.5 g of DPM to the resulting solution and stirring.

(3) Solution A3
Solution A3 was prepared by dissolving 0.143 g of AN1 in 3.5 g of DMI under a nitrogen atmosphere, then adding 1.0 g of 2,3-BD and 0.5 g of DPM to the resulting solution and stirring.

(4) Solution A4
Solution A4 was prepared by dissolving 0.068 g of F4TCNQ in 5 g of DMI, and stirring the resulting solution.

As shown in FIG. 1, it is apparent that the varnish of Working Example 1-1 has a characteristic absorption at wavelengths of from 600 to 1,000 nm. As shown in FIGS. 2 and 3, it is apparent that the solutions prepared by dissolving F4TCNQ in a mixed solvent (DMI:2,3-BD: DPM=70:20:10) or in DMI also have similar characteristic absorptions.

On the other hand, as shown in FIG. 1, the varnish of Comparative Example 1-1 does not have an absorption like that described above at wavelengths of 600 to 1,000 nm.

Also, as shown in FIG. 2, solutions prepared by dissolving in a mixed solvent phosphotungstic acid alone or an arylamine derivative (AN1) alone without adding F4TCNQ did not have an absorption like that described above at wavelengths of 600 to 1,000 nm.

These facts suggest that F4TCNQ and DMI interact within the varnish to form a certain type of complex.

Two conspicuous peaks (between 750 to 800 nm, and between 850 to 900 nm) are observable in the absorption spectrum for the varnish of Working Example 1-1 at from 600 to 1,000 nm. The wavelengths of these respective peaks are respectively 762 nm and 866 nm.

[4] Fabrication and Evaluation of Single-Layer Devices

A glass substrate with dimensions of 25 mm×25 mm×0.7 mm (t) and having indium-tin oxide patterned on the surface to a film thickness of 150 nm (abbreviated below as a "ITO substrate") was used as the substrate for evaluating the electrical characteristics. The ITO substrate was used after removing impurities on the surface with an O$_2$ plasma cleaning system (150 W, 30 seconds).

Working Example 2-1

The varnish obtained in Working Example 1-1 was coated onto an ITO substrate using a spin coater and was subsequently dried for 1 minute at 80° C. and then, in open air, was baked for 15 minutes at 230° C., thereby forming a uniform 30 nm thin film on an ITO substrate.

Next, using a vapor deposition system, an aluminum thin film was formed on the ITO substrate on which a thin film had been formed, thereby giving a single-layer device. The thickness of the aluminum thin film was set to 120 nm and vapor deposition was carried out at a degree of vacuum of $1.3 \times 10^{-3}$ Pa and a deposition rate of 0.2 nm/s.

To prevent the device characteristics from deteriorating due to the influence of oxygen, moisture and the like in air, the device was sealed with sealing substrates, following which the characteristics were evaluated. Sealing was carried out by the following procedure. The device was placed between sealing substrates in a nitrogen atmosphere having an oxygen concentration of not more than 2 ppm and a dew point of not more than −85° C., and the sealing substrates were laminated together using an adhesive (MORESCO Moisture Cut WB90US(P), from Moresco Corporation). At this time, a desiccant (HD-071010W-40, from Dynic Corporation) was placed, together with the device, within the sealing substrates. The laminated sealing substrates were irradiated with UV light (wavelength, 365 nm; dosage, 6,000 mJ/cm$^2$), then annealed at 80° C. for 1 hour to cure the adhesive.

Comparative Example 2-1

Aside from using the varnish obtained in Comparative Example 1-1 instead of the varnish obtained in Working Example 1-1, a single-layer device was fabricated in the same way as in Working Example 2-1.

The current density at a driving voltage of 3V was measured for the single-layer devices thus manufactured. The results are shown in Table 1.

TABLE 1

|  | Current density (mA/cm$^2$) |
|---|---|
| Working Example 2-1 | 920 |
| Comparative Example 2-1 | 80 |

As shown in Table 1, compared with the thin-film produced from the varnish in the Comparative Example in which F4TCNQ does not form a complex, the thin film produced from the varnish in the Working Example in which F4TCNQ and DMI form a complex had an excellent charge transportability.

[5] Fabrication and Evaluation of Organic EL Devices

Working Example 3-1

Using the varnish obtained in Working Example 1-1, a uniform 30 nm thin film was formed on an ITO substrate by the same method as in Working Example 2-1.

Next, using a vapor deposition system (degree of vacuum, 1.0×10$^{-5}$ Pa), thin-films of N,N'-di(1-naphthyl)-N,N'-diphenylbenzidine (α-NPD), tris(8-quinolinate) aluminum(III) (Alq$_3$), lithium fluoride and aluminum were successively deposited on the ITO substrate on which a thin-film had been formed, thereby giving an organic EL device. At this time, vapor deposition was carried out at a rate of 0.2 nm/s for the α-NPD, Alq$_3$ and aluminum, and at a rate of 0.02 nm/s for the lithium fluoride. The film thicknesses were set to respectively 30 nm, 40 nm, 0.5 nm and 100 nm.

The organic EL device was sealed with sealing substrates in the same way as in Working Example 2-1.

Comparative Example 3-1

Aside from using the varnish obtained in Comparative Example 1-1 instead of the varnish obtained in Working Example 1-1, an organic EL device was fabricated by the same method as in Working Example 3-1.

The driving voltage, current density and current efficiency were measured when each of the devices fabricated above were made to emit light at a brightness of 5,000 cd/m$^2$. The results are shown in Table 2.

TABLE 2

|  | Driving voltage (V) | Current density (mA/cm$^2$) | Current efficiency (cd/A) |
|---|---|---|---|
| Working Example 3-1 | 9.38 | 19.5 | 25.7 |
| Comparative Example 3-1 | 9.89 | 25.3 | 20.8 |

As shown in Table 2, compared with the device in Comparative Example 3-1, the device in Working Example 3-1 had a low driving voltage and also had a high current efficiency.

As demonstrated above, by using a thin film obtained from a charge-transporting material of the invention as the hole-injecting layer in an organic EL device, it is possible to lower the driving voltage of the organic EL device.

The invention claimed is:

1. A charge-transporting material comprising:
   a charge transporting substance:
   a halotetracyanoquinodimethane:
   a complexing agent having the ability to form a complex with the halotetracyanoquinodimethane, wherein the halotetracyanoquinodimethane and the complexing agent form a complex: and
   a heteropolyacid.

2. The charge-transporting material of claim 1, wherein the complexing agent comprises an amide compound.

3. The charge-transporting material of claim 2, wherein the amide compound is 1,3-dimethyl-2-imidazolidinone.

4. The charge-transporting material of any one of claims 1 to 3, wherein the halotetracyanoquinodimethane is 2,3,5,6 tetrafluoro-7,7,8,8-tetracyanoquinodimethane.

5. The charge-transporting material of claim 1, wherein the charge-transporting substance is a charge transporting oligomer.

6. A charge-transporting thin film produced using the charge-transporting material of claim 1.

7. An organic electroluminescent device comprising the charge-transporting thin film of claim 6.

8. A method for producing a charge-transporting thin film, which method comprises the steps of applying the charge transporting material of claim 1 onto a substrate, and drying the applied material.

9. A method for enhancing the charge transportability of a charge-transporting thin film comprising the steps of:
   forming a composition comprising a charge-transporting substance, a halotetracyanoquinodimethane, and a heteropolyacid; and
   adding to the composition a complexing agent having the ability to form a complex with the halotetracyanoquinodimethane.

10. A method for enhancing the charge transportability of a charge-transporting thin film comprising the steps of:
    forming a composition comprising a charge-transporting substance, a halotetracyanoquinodimethane, a heteropolyacid and an organic solvent,
    wherein at least some portion of the organic solvent comprises a complexing agent having the ability to form a complex with the halotetracyanoquinodimethane.

11. The charge transportability-enhancing method of claim 9 or 10, wherein the complexing agent is an amide compound.

12. The charge-transporting material of claim 1, wherein the complexing agent consists of an amide compound.

* * * * *